(12) United States Patent
Nakamura

(10) Patent No.: US 11,850,783 B2
(45) Date of Patent: Dec. 26, 2023

(54) MANUFACTURING METHOD AND MANUFACTURING APPARATUS FOR LAMINATE

(71) Applicant: ZUIKO CORPORATION, Osaka (JP)

(72) Inventor: Hideyuki Nakamura, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 333 days.

(21) Appl. No.: 17/282,763

(22) PCT Filed: Oct. 28, 2019

(86) PCT No.: PCT/JP2019/042210
§ 371 (c)(1),
(2) Date: Apr. 4, 2021

(87) PCT Pub. No.: WO2020/090754
PCT Pub. Date: May 7, 2020

(65) Prior Publication Data
US 2022/0009142 A1     Jan. 13, 2022

(30) Foreign Application Priority Data
Oct. 29, 2018    (JP) ................................ 2018-202622

(51) Int. Cl.
    *B29C 48/00*        (2019.01)
    *B29C 48/154*      (2019.01)
              (Continued)

(52) U.S. Cl.
    CPC ...... *B29C 48/0021* (2019.02); *B29C 48/0022* (2019.02); *B29C 48/08* (2019.02);
              (Continued)

(58) Field of Classification Search
CPC . B29C 48/0021; B29C 48/0022; B29C 48/08; B29C 48/154; B29C 48/21;
(Continued)

(56) References Cited

U.S. PATENT DOCUMENTS 4,348,346 A * 9/1982 Thompson .............. B29C 48/12
                                                 264/173.17
4,885,457 A * 12/1989 Au ..................... B29C 48/0022
                                                     219/505
(Continued)

FOREIGN PATENT DOCUMENTS

| JP | H10-29259 A | 2/1998 |
|----|----|----|
| JP | H10-278182 A | 10/1998 |
| JP | 2014037105 A | 2/2014 |

OTHER PUBLICATIONS

International Search Report for corresponding Application No. PCT/JP2019/042210, dated Dec. 10, 2019.

*Primary Examiner* — Jeffrey M Wollschlager
(74) *Attorney, Agent, or Firm* — Renner, Otto, Boisselle & Sklar, LLP

(57) ABSTRACT

In a manufacturing method, resin in a molten state which becomes a film raw material is caused to hang down from a discharge port of a discharger and the film-like film raw material is continuously discharged, a sheet is conveyed along a sheet pass line, a tip part of the film raw material is formed by cutting and removing an initially formed part of the initially formed film raw material, the tip part is overlapped on the sheet on the sheet pass line, the sheet and the film raw material in a mutually overlapping state are conveyed along the sheet pass line, and the sheet and the film raw material are introduced to a joining part from the sheet pass line.

7 Claims, 5 Drawing Sheets

(51) Int. Cl.
*B29C 48/08* (2019.01)
*B29C 48/21* (2019.01)
*B29C 55/02* (2006.01)
*B29C 55/06* (2006.01)
*B29C 55/18* (2006.01)

(52) U.S. Cl.
CPC ............ *B29C 48/154* (2019.02); *B29C 48/21* (2019.02); *B29C 55/023* (2013.01); *B29C 55/06* (2013.01); *B29C 55/18* (2013.01)

(58) Field of Classification Search
CPC ....... B29C 55/023; B29C 55/06; B29C 55/18; B29C 2793/00; B29C 66/83415; B29C 66/1122; B29C 66/433; B29C 66/7294; B29C 66/83411; B29C 65/086; B29C 48/914; B29C 48/305; B29K 2701/12; B29K 2995/0046; A61F 13/15593; A61F 13/15739; A61F 13/4902; B29L 2031/4878; B32B 37/203; B32B 37/206; B32B 38/0004; B32B 2555/02
See application file for complete search history.

(56) References Cited

U.S. PATENT DOCUMENTS

| | | | |
|---|---|---|---|
| 6,238,767 B1 | 5/2001 | McCormack | |
| 2008/0115878 A1* | 5/2008 | Mullet | B29C 44/326 156/196 |
| 2008/0157424 A1* | 7/2008 | Fujii | B29C 48/21 264/171.15 |
| 2009/0107623 A1* | 4/2009 | Davidson | B29C 44/326 156/252 |
| 2014/0322463 A1* | 10/2014 | Bashir | B29C 55/06 428/221 |

* cited by examiner

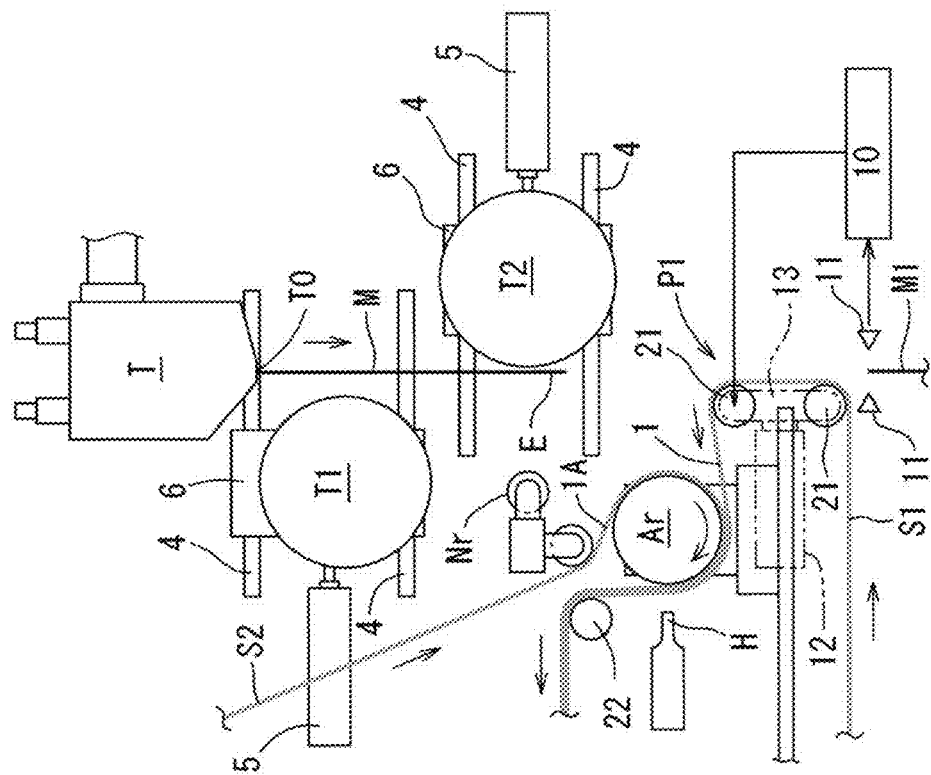
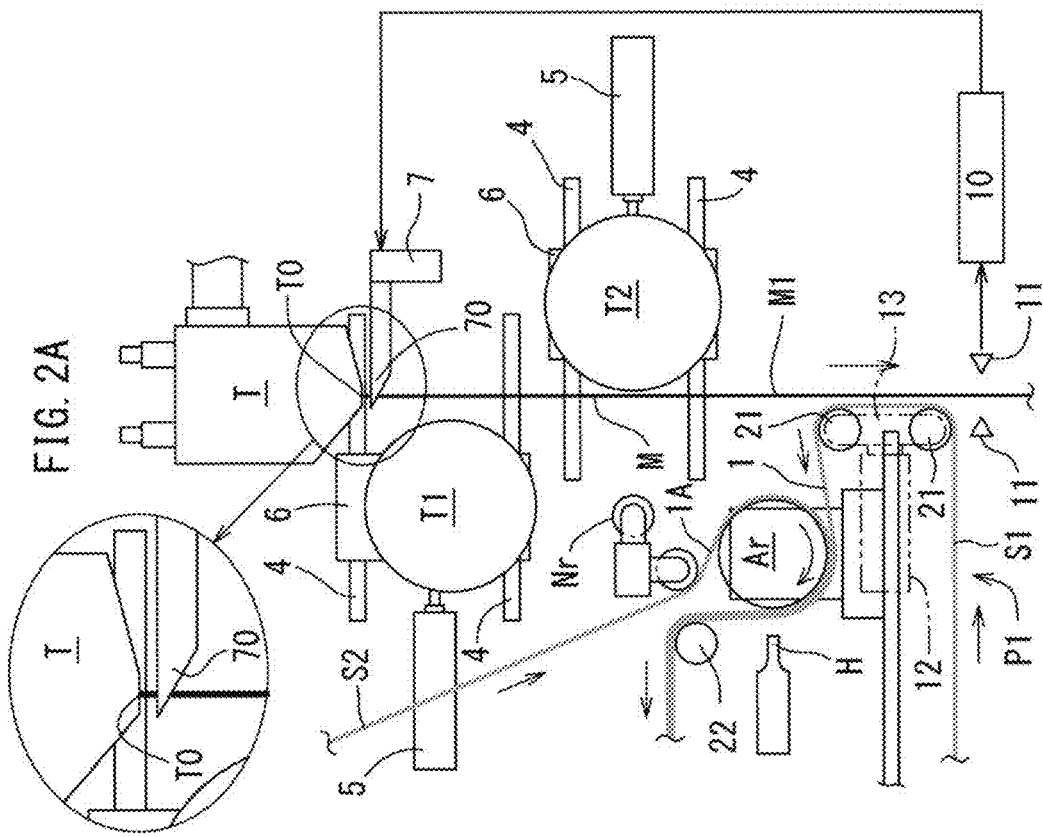
FIG. 2A
FIG. 2B

MANUFACTURING METHOD AND MANUFACTURING APPARATUS FOR LAMINATE

TECHNICAL FIELD

The present invention relates to a manufacturing method and a manufacturing apparatus for laminate usable in a part of a disposable absorbent article such as a disposable diaper and the like.

BACKGROUND ART

In recent years, a structure in which an elastomer film is sandwiched between a pair of nonwoven fabric sheets has been proposed as such a laminate. Further, it has been proposed to produce the film from resin in a molten state in a production line for this laminate (see patent literature 1).

CITATION LIST

Patent Literature

Patent Literature 1: JP H10-29259A (FIGS. 4 and 5)

SUMMARY OF INVENTION

In the above conventional technique, the resin in the molten state is extruded into a film from a discharge port, the elastomer film is produced by cooling a pre-elastomer having adhesiveness in the form of the extruded film and, thereafter, the elastomer film is laminated on the nonwoven fabric sheet.

In such a production line, when the production of laminates is temporarily stopped and, thereafter, the production is resumed, a pass line for the pre-elastomer film needs to be formed. However, conventionally, a person has formed the pass line for the pre-elastomer by pulling a tip part of the adhesive pre-elastomer.

For example, when the elastomer film is produced and used as an elastic member in the production line for absorbent articles, the line is often stopped due to a change in the size of the products to be produced and the like, and the operation as described above is often performed.

Further, the pre-elastomer is non-uniform at the restart of operation. Thus, a stable elastomer film cannot be obtained. If such a non-uniform elastomer film is used as an elastic member, a yield is reduced and more material is wasted.

The present invention aims to provide a manufacturing method and a manufacturing apparatus for laminate capable of improving a yield, in a production line for laminate including a film manufacturing process, by introducing a uniform thermoplastic film into a pass line after the production line is stopped.

A manufacturing method of the present invention is a manufacturing method for manufacturing a laminate W by laminating a thermoplastic film F on a sheet S1 at a joining part (a joining area, a converging point) after a pass line forming process of forming a pass line for a film-formed film raw material M, the film raw material M becoming the thermoplastic film F, the pass line forming process including:

a hanging-down step of causing a resin in a molten state to hang down from a discharge port TO of a discharger T, the resin becoming the film raw material M, and the hanging-down step continuously discharging the film raw material M;

a first conveying step of conveying the sheet S1 along a sheet pass line 1;

a forming step of forming a tip part E of the film raw material M by cutting and removing an initially formed part M1 of the film raw material M, the initially formed part M1 being removed from the tip part E;

a second conveying step of conveying the sheet S1 and the film raw material M after the tip part E overlaps the sheet S1 on the sheet pass line 1, the second conveying step conveying the sheet S1 and the film raw material M in a mutually overlapping state along the sheet pass line 1; and an introducing step of introducing the sheet S1 and the film raw material M in the mutually overlapping state to the joining part from the sheet pass line 1.

On the other hand, a manufacturing apparatus of the present invention is a manufacturing apparatus for manufacturing a laminate W laminating a thermoplastic film F on a sheet S1 at a joining part (a joining area, a converging point) after a pass line forming process of forming a pass line for a film-formed film raw material M, the film raw material M1 becoming the thermoplastic film F, the manufacturing apparatus including:

a discharger T for causing a resin in a molten state to hang down from a discharge port TO, the resin becoming the film raw material M, and the discharger T continuously discharging the film-formed film raw material M;

a cutter 7 for cutting off an initially formed part M1 of the film raw material M so as to form a tip part E of the film raw material M, the initially formed part M being removed from the tip part E;

a sheet pass line 1 for receiving the tip part E of the film raw material M with the sheet S1 and conveying the sheet S1 and the film raw material M in a mutually overlapping state after the tip part E overlaps the sheet S1; and the joining part configured such that the sheet S1 and the film raw material M in the mutually overlapping state are introduced to the joining part from the sheet pass line 1.

In the present invention, the thermoplastic film F may be an elastomer film F and the film raw material M may be a film-formed (a film-like) pre-elastomer M.

In the present invention, the initially formed part M1 of the film-like pre-elastomer M hanging down from the discharge port is cut and removed. Thus, the homogeneous and stable tip part E of the pre-elastomer M can be conveyed together with the sheet and introduced to the joining part for producing the laminate. Therefore, the waste of the material can be prevented and a yield is improved.

In the present invention, the thermoplastic film may be a plastomer film having low stretchability. If the thermoplastic film is an elastomer film, the elastomer film may be a film having such high stretchability that a length is expanded by two to several folds and is restored to an initial length.

In the present invention, the resin in the molten state means resin discharged in the form of a film from a discharge port of a T die or the like at a temperature equal to or higher than a softening point of thermoplastic resin (e.g. thermoplastic elastomer).

The thermoplastic elastomer is a polymer material which is softened by heating and deformed by an external force, but exhibits rubber elasticity at a room temperature. The pre-elastomer M means a membrane-like (film-like) thermoplastic elastomer having properties close to those of a non-elastic liquid immediately after coming out in a molten state from a discharge port. For example, a polyethylene copolymer can be employed as the thermoplastic elastomer (see JP H10-29259A).

BRIEF DESCRIPTION OF THE DRAWINGS

FIGS. 2A and 2B are layout diagrams respectively showing one embodiment of a process of cutting and removing the pre-elastomer.

DESCRIPTION OF EMBODIMENTS

Figure 1B:
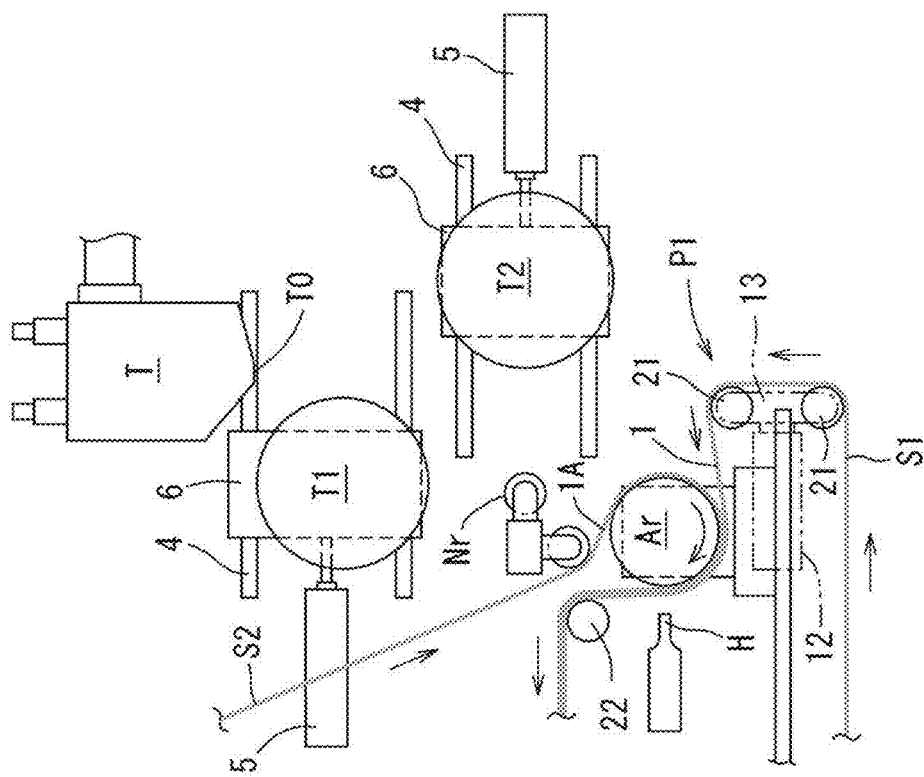
FIGS. 1A and 1B are layout diagrams respectively showing one embodiment of a method and an apparatus for producing an elastomer at the restart of operation.

Preferably, the forming step further includes a cutting step of cutting the initially formed part M by moving a blade 70 in a width direction D of the pre-elastomer M, and a removing step of removing the cut initially formed part M1.

In this case, the pre-elastomer M is unlikely to adhere to the blade 70 and the adhesive pre-elastomer M could be satisfactorily cut unlike cutting by a Thomson blade.

Note that the blade 70 may be a sharp mechanical blade configured to cut the pre-elastomer M by contacting the pre-elastomer M, but may a blade which can cut the pre-elastomer M without contacting the pre-elastomer M1 like a laser.

Preferably, the forming step includes a retracting step of retracting the sheet pass line 1 in advance to a retracted position P1 where the initially formed part M1 does not contact the sheet pass line 1, a projecting step of causing the sheet pass line 1 to project to a contact position P2 where the tip part E of the pre-elastomer M contacts the sheet S1 on the sheet pass line 1 and the tip part E and the sheet S1 overlap each other, and a removing step of removing the cut initially formed part M1 before the projecting step and after the retracting step.

In this case, the initially formed part M1 can be removed with the sheet pass line 1 retracted and the initially formed part M1 would be easily removed.

Preferably, the removing step is performed by the cut initially formed part M1 falling without contacting the sheet pass line 1. Note that since a falling speed of the initially formed part M1 is accelerated by gravity, the falling speed would be larger than a resin discharging speed from the discharge port TO.

If the initially formed part M1 falls to be removed in this way, an apparatus for removing the initially formed part M1 is not necessary. Note that the initially formed part M1 may be wound on a roller.

Preferably, the first conveying step is performed by conveying the sheet S1 in a lateral or oblique lateral direction below the discharge port TO after the projecting step, and the manufacturing method further includes a receiving step of receiving the tip part E of the pre-elastomer M discharged and hanging down from the discharge port TO with the sheet S1 in the sheet pass line 1 after the projecting step.

In this case, the tip part E of the film-like pre-elastomer M hanging down from the discharge port can be received by the sheet conveyed in the lateral or oblique lateral direction. Thus, the tip part E of the pre-elastomer M can be conveyed together with the sheet and automatically introduced to the joining part for generating the laminate. Therefore, the film pass line can be easily formed.

Preferably, the manufacturing method includes a bonding step of producing the laminate W by laminating the elastomer film F obtained by solidifying the pre-elastomer M by bonding it to the sheet S1 at the joining part after the pass line forming process.

In this case, the elastomer film F and the sheet S1 are bonded and laminated at the joining part in charge of the bonding step.

Preferably, the sheet S1 and the elastomer film F are conveyed in an overlapping manner along an outer peripheral surface of a bonding roll Ar serving as the joining part and the bonding step is performed on the bonding roll Ar.

In this case, the bonding step is performed on a bonding roll such as an anvil roll.

The preferred manufacturing apparatus further includes a control device 10 for detecting the removal of the cut initially formed part M1 and moving the sheet pass line 1 at the retracted position P1 to the contact position P2.

In this case, the initially formed part M1 can be removed with high reliability without contacting the sheet pass line 1.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiment

The present invention will be understood more clearly from the following description of preferred embodiments taken in conjunct on with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Hereinafter, one embodiment of the present invention is described on the basis of the drawings. First, a steady manufacturing method and apparatus is described.

FIG. 5 shows a steady operation for continuously producing a laminate W. In FIG. 5, a discharger T is a known extrusion molding machine called a T-die, and a thermoplastic elastomer (resin) in a molten state is temporarily stored in the T die. The T die continuously produces pre-elastomer M by discharging the resin in the molten state, which becomes the pre-elastomer (an example of a film raw material) M, in the form of a film from a discharge port TO thereof.

The pre-elastomer M discharged from the discharge port TO is temporarily cooled by being wound on the outer peripheral surface of a first cooling roll T1, and conveyed toward the outer peripheral surface of a second cooling roll T2 below the first cooling roll T1. In this way, the pre-elastomer M is substantially solidified and has elasticity (stretchability) as an elastomer film (an example of the thermoplastic film) F.

The pre-elastomer M which moved toward the second cooling roll T2 is secondarily cooled by the outer peripheral surface of the second cooling roll T2. In this way, the pre-elastomer M is completely solidified to become the elastomer film (elastic film) F.

The secondarily cooled elastomer film F moves toward a bonding roll Ar after being sandwiched between the second cooling roll T2 and a nip roll Nr. The bonding roll Ar has a larger circumferential speed. (conveying speed) than the second cooling roll T2. Thus, the elastomer film F is stretched in a conveying direction between the nip roll Nr and the bonding roll Ar.

As just described, the molten resin becomes the elastomer film (thermoplastic film) F by way of a state of the pre-elastomer (film raw material) M. Here, at which points of time a transition from the molten resin as a substance to the pre-elastomer M and a transition from the pre-elastomer M to the elastomer film F are exhibited differ depending on a glass-transition temperature, a thickness of the resin and a room temperature, and are not certain.

For example, the molten resin becomes the pre-elastomer M and looks like a solid substance at a glance immediately after coming out from the discharge port TO, but may have properties close to those of a non-elastic liquid.

On the other hand, the pre-elastomer M changes to the elastomer film F in a part pulled on a side downstream of the nip roll Nr, but this timing differs when the pre-elastomer M becomes the elastomer film F after contacting the second cooling roll T2 upstream of the nip roll Nr, when the pre-elastomer M becomes the elastomer film F after contacting the first cooling roll T1, and the like.

Accordingly, a film pass e 3 means this conveyance path in a state where the film is at least partially the pre-elastomer (film raw material) M.

On the other hand, first and second sheets S1, S2 made of nonwoven fabric are supplied to the bonding roll Ar. The first and second sheets S1, S2 are supplied to the bonding roll Ar along a first sheet pass line 1 and a second sheet pass line 1A, respectively.

The elastomer film F is introduced to the bonding roll Ar while being sandwiched by the pair of sheets S1, S2, and the pair of sheets S1, S2 and the elastomer film F are bonded to and laminated with each other on the bonding roll Ar by an ultrasonic horn H to produce the laminate W.
Note that the laminate W may be produced not by ultrasonic bonding by the horn H, but by heat welding by a heating roll.

Although the laminate W is continuously produced, the production may be temporarily stopped due to a size change or the like. In this case, the film pass line shown in FIGS. 1A to 5A is formed for a new elastomer film F.

Next, the manufacturing apparatus is described.
Each cooling roll T1, T2 of FIG. 4B is rotatably supported on a corresponding slide base 6 and moved in a horizontal direction as shown in FIGS. 4B and 5A by a cylinder 5 along a guider 4. Each cooling roll T1, T2 is rotationally driven at a circumferential speed Vs by an unillustrated motor. On the other hand, the bonding roll Ar is rotationally driven at a circumferential speed V larger than the circumferential speed Vs by an unillustrated motor.

Figure 1A:
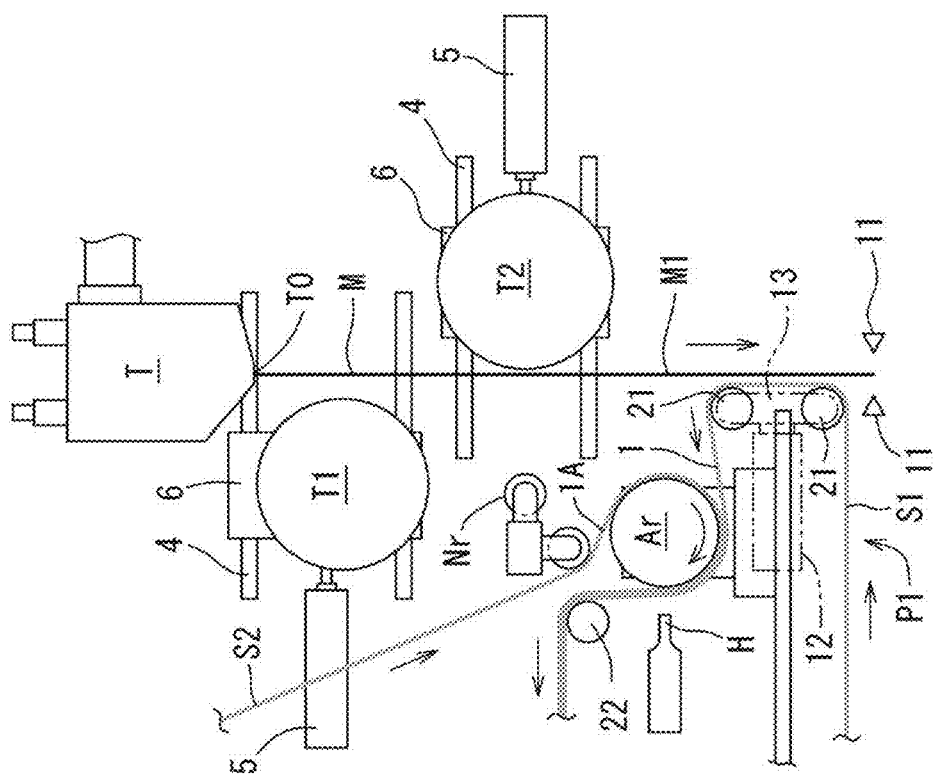

To form the film pass line 3 (FIG. 5A) anew, each cooling roll T1, T2 is first retracted by the cylinder 5 as shown in FIG. 1A. By this retraction, the pre-elastomer M of FIG. 1B newly discharged and hanging down from the discharge port TO of the discharger T does not contact each cooling roll T1, T2. Specifically, each cooling roll T1, T2 is provided movably to contact with and away from the hanging-down pre-elastomer M of FIG. 1B.

Figure 3A:
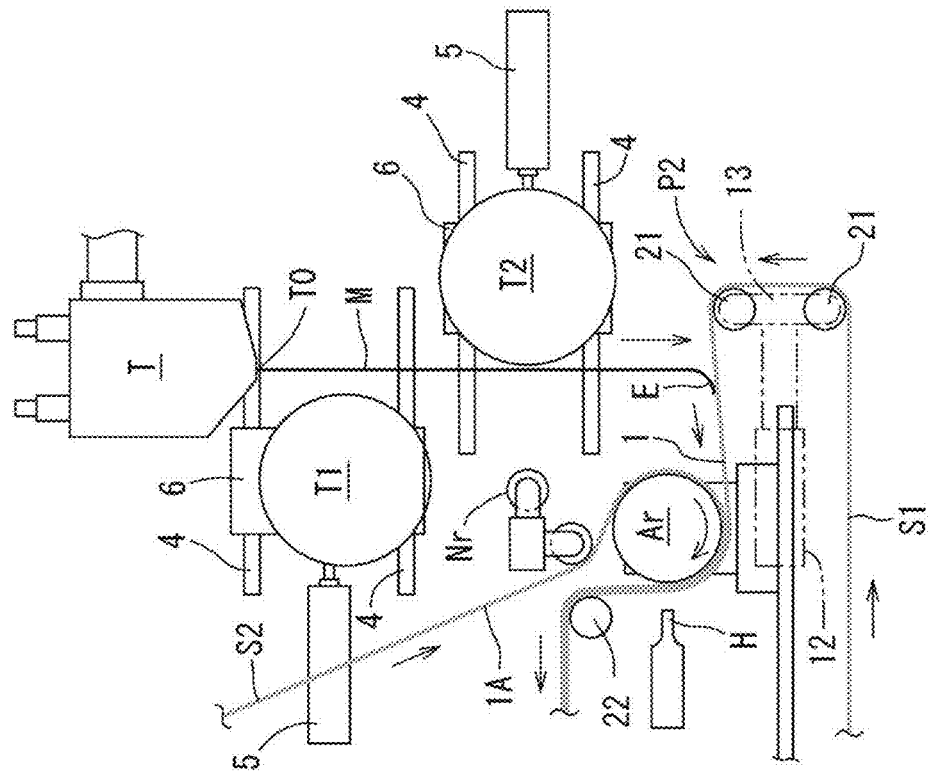
FIGS. 3A and 3B are layout diagrams respectively showing one embodiment of a process of forming a film pass line.
Figure 3B:
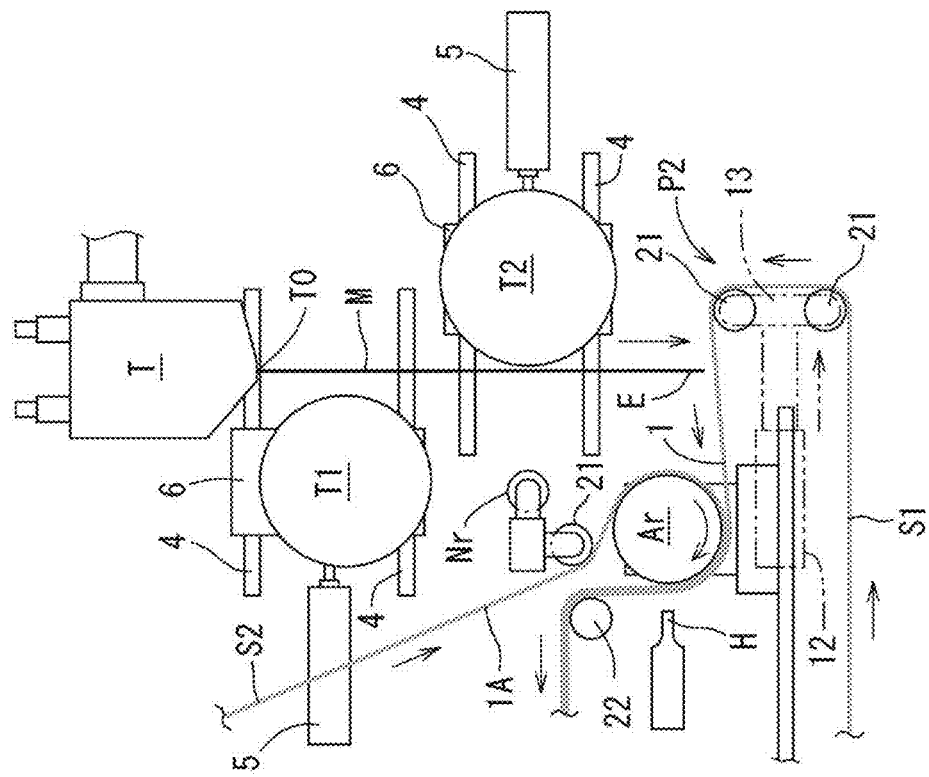

In FIG. 3A, each of the pass lines 1, 1A for the first and second sheets S1, S2 are formed by one or more first rolls 21, the bonding roll Ar, and the like for conveying the sheets S1, S2. A pass line 2 for the laminate W of FIG. 5A is formed by the bonding roll Ar, second rolls 22, and the like for conveying the laminate W. The film pass line 3 is formed by the first cooling roll T1 and the second cooling roll T2 for conveying the pre-elastomer M or elastomer film F and the bonding roll Ar and the like for bonding the elastomer film F to the both sheets S1, S2. The pass line 2 for the laminate W of FIG. 5A is formed so that the pair of sheet pass lines 1, 1A and the film pass line 3 join at the bonding roll Ar.

In this embodiment, a cutter 7 of FIG. 2A is provided. This cutter 7 cuts an initially formed part M1 of the initially formed pre-elastomer M. In this way, a tip part E of the pre-elastomer M of FIG. 2B having the initially formed part M1 removed is formed. A cutting position by the cutter 7 is preferably near the discharge port TO so that there is a sufficient distance (interval) between this tip part E and the initially formed part M1 to be discarded and the cutting position, for example, would be preferably above the lower end of the first cooling roll T1.

Figure 5B:
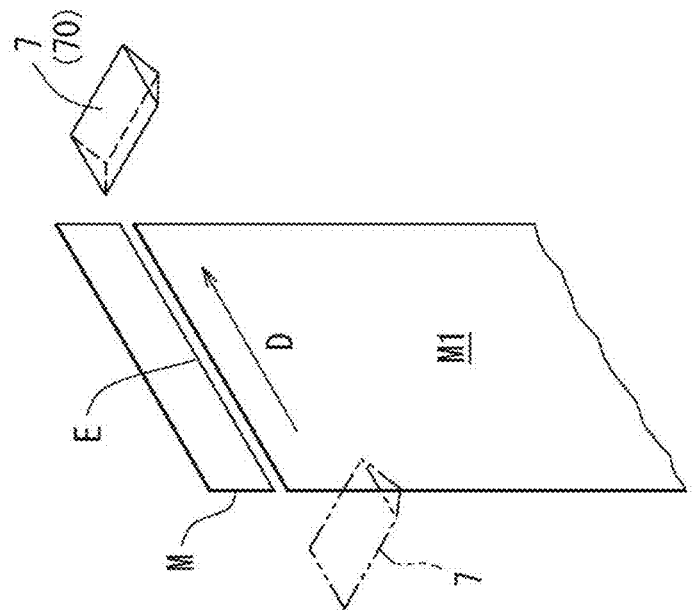
FIG. 5A is a schematic layout diagram showing one embodiment of a manufacturing method and a manufacturing apparatus for laminate of the present invention and FIG. 5B is a schematic perspective view showing an example of a pre-elastomer cutting method.
Figure 5A:
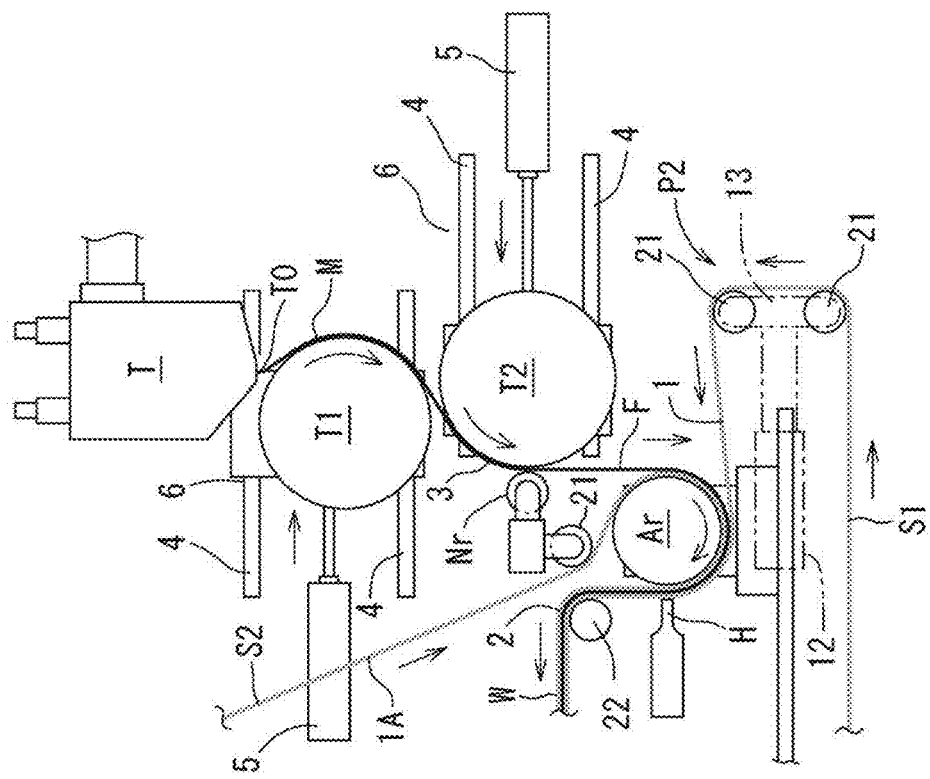

As shown in FIG. 5B, the cutter 7 may include a blade 70 configured to move in a width direction D of the pre-elastomer M to cut off the initially formed part M1. For example, the blade 70 may be reciprocally moved by a motor via a wire.

As shown in FIGS. 3A and 2B, in this embodiment, a moving device 12 for the sheet pass line 1 is provided. The moving device 12 moves the sheet pass line 1 between a retracted position P1 of FIG. 2B and a contact position P2 of FIG. 3A by moving a pair of the first rolls 21 supported on a frame 13, for example, by air cylinders. At the retracted position P1 of FIG. 2B, the sheet pass line 1 is not in contact with the initially formed part M1. On the other hand, at the contact position P2 of FIGS. 3A to 4A, the tip part E of the pre-elastomer M contacts the first sheet S1 on the sheet pass line 1 to form double overlapping layers.

In FIGS. 2A and 2B, this manufacturing apparatus may include a control device 10. The control device 10 detects the removal of the cut initially formed part M by a signal from a detector 11 such as a photoelectric switch and moves the sheet pass line 1 at the retracted position P1 to the contact position P2 of FIG. 3A by the moving device 12.

Next, a process of forming the film pass line 3 necessary prior to the production of a new laminate W of FIG. 5A is described.

To form the film pass line 3 anew, the first cooling roll T1, the second cooling roll T2 and the first sheet pass line 1 are returned to initial states as shown in FIG. 1A from states of the steady operation of FIG. 5A.

Specifically, prior to the film pass line forming process, the moving device 12 of FIG. 5A first contracts (operates) to retract the sheet pass line 1 at the contact position P2 to the retracted position P1 as shown in FIG. 1A. At this retracted position P1, the sheet pass line 1 does not contact the pre-elastomer M hanging down from the discharge port TO of the discharger T of FIG. 1B.

On the other hand, as shown in FIG. 1B, in the film pass line forming process, the first cooling roll T1 is arranged to face one side surface of the pre-elastomer M hanging down from the discharge port TO. The second cooling roll T2 (pressing roll) is arranged to face the other side surface opposite to the one side surface. Thus, the pre-elastomer M discharged from the discharger T hangs straight down between the first cooling roll. T1 and the second cooling roll T2 without contacting the first cooling roll T1 and the second cooling roll T2.

Specifically, the resin in the molten state, which becomes the pre-elastomer M of FIG. 1B, hangs down from the discharge port TO of the discharger T, and the film-like pre-elastomer M is continuously discharged. In this way, the pre-elastomer M hangs down on one flat plane along a vertical plane without contacting each roll T1, T2, Ar.

After the discharge of the pre-elastomer M, the initially formed part M1 of the pre-elastomer M. of FIG. 1B is detected by the detector 11. After this detection, the cutter 7 may operate in response to a command from the control device 10 of FIG. 2A, for example, upon the elapse of a certain time. Specifically, as shown in FIG. SB, the blade 70 moves in the width direction D of the pre-elastomer M to cut the initially formed part M1.

After this cutting, the pre-elastomer M in a stable state is produced from the discharge port TO of FIG. 2B. On the other hand, the cut initially formed part M1 falls to be removed without contacting the sheet pass line 1.

Further, after the cutting, the control device 10 may detect the rear end of the initially formed part M1 by the detector 11. Thereafter, the control device 10 having detected the rear end of the initially formed part M1 outputs a movement command to the moving device 12 and, as shown in FIG. 3A, the moving device 12 operates and the sheet pass line 1 projects to the contact position P2. At this contact position P2, the sheet pass line 1 can receive a new tip part E of the pre-elastomer M after the cutting.

On the other hand, the first sheet S1 is conveyed along the first pass line 1 for first sheet in a lateral or oblique lateral direction immediately below the discharge port TO of FIG. 3A. In a state where the first sheet S1 is conveyed, the tip part E of the pre-elastomer M discharged and hanging down from the discharge port TO is received with the sheet S1 as shown in FIG. 31B.

Figure 4A:
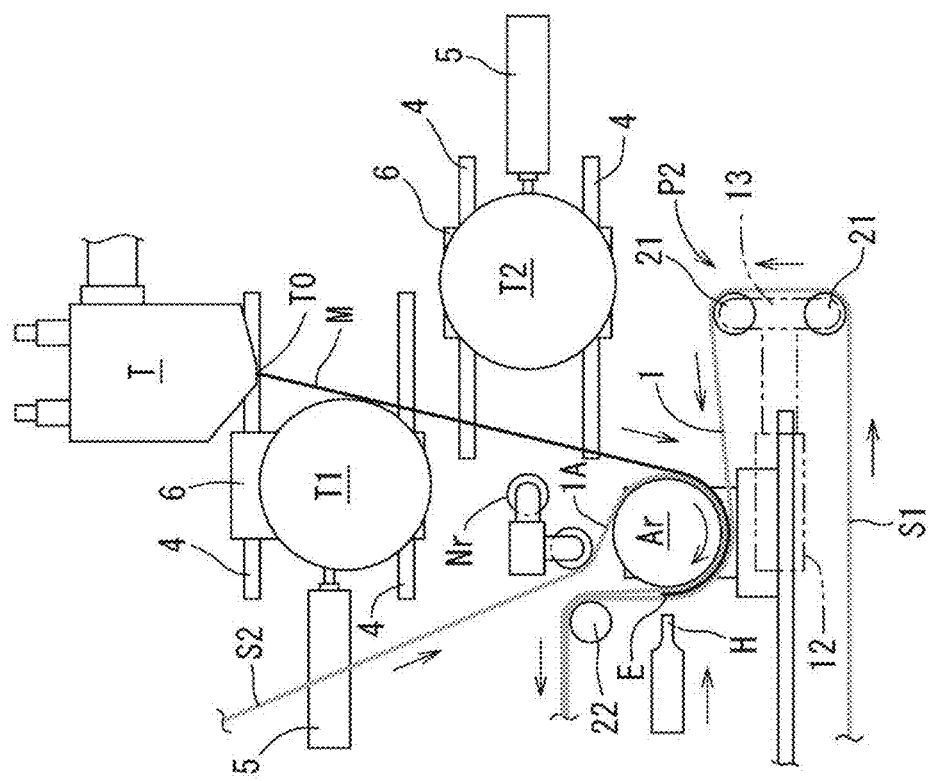
FIGS. 4A and 4B are layout diagrams showing one embodiment of the process of forming the film pass line.
Figure 4B:
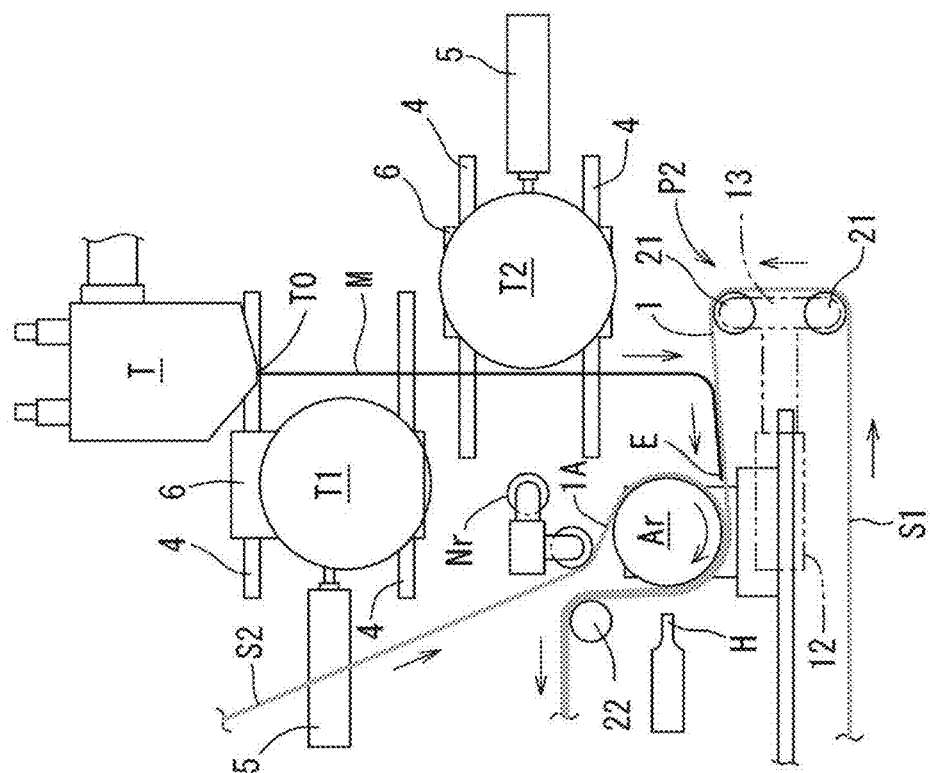

After this receiving, the tip part E is overlapped on the first sheet S1 and the first sheet S1 and the pre-elastomer M in a mutually overlapping (doubled) state are conveyed along the first pass line 1 for first sheet as shown in FIG. 4A. The first sheet S1 and the pre-elastomer M in the mutually overlapping state are introduced along the outer peripheral surface of the bonding roll Ar (an example of a bonding part (joining part)) from the first pass line 1 for first sheet as shown in FIG. 4B.

By this introduction, the pre-elastomer M starts to be linearly conveyed from the discharge port TO to contact the outer peripheral surface of the bonding roll Ar as shown in FIG. 4B. Thereafter, as shown in FIG. 5A, the first cooling roll 11 and the second cooling roll T2 are moved toward the pre-elastomer M.

In this way, the pre-elastomer M continuously discharged from the discharge port TO contacts the outer peripheral surfaces of the first cooling roll T1 and the second cooling roll T2, and the film pass line 3 in which the elastomer film F is sandwiched between the second cooling roll T2 and the nip roll Nr is formed (completed).

In the film pass line 3, a first cooling step is performed in which the pre-elastomer M is wound on the outer peripheral surface of the first cooling roll T1 to be cooled. If a manufacturing apparatus includes at least one cooling roll, a film pass line is formed when the pre-elastomer M contacts this cooling roll.

Further, as described above, the pressing roll, which is the second cooling roll T2, moves in a direction intersecting the hanging direction of the pre-elastomer M to increase a distance over which the pre-elastomer M contacts the first cooling roll T1. The pressing roll is the second cooling roll T2, and the pre-elastomer M cooled by the first cooling roll T1 is further cooled by the second cooling roll T2. In this way, the pre-elastomer is solidified to become the elastomer film F.

Note that each cooling roll is for cooling the molten resin or film and may internally include a flow passage for cooling a roll surface by the flow of a refrigerant.

On the other hand, the nip roll Nr sandwiches the elastomer film F on a side further upstream than the bonding roll Ar. After the film pass line 3 is formed, the elastomer film F before being bonded to the both sheets S1, S2 is stretched in the conveying direction because the conveying speed V of the elastomer film on the bonding roll Ar is larger than the conveying speed Vs of the elastomer film F on the nip roll Nr. In this way, a pre-stress (tension) is applied to the elastomer film F.

After the process of forming the film pass line 3 of FIG. 5A, the horn H repeatedly applies ultrasonic vibration to the bonding roll Ar to bond the elastomer film F to the first and second sheets S1, S2 on the bonding roll Ar, whereby the laminate W is produced. Specifically, the both sheets S1, S2 and the elastomer film F are conveyed in an overlapping manner along the outer peripheral surface of the bonding roll Ar and the horn H applies ultrasonic vibration to the bonding roll Ar, whereby ultrasonic energy is applied to the both sheets S1, S2 and the elastic film F, and the nonwoven fabric sheets and the elastomer film are bonded and laminated.

Note that the bonding may be, for example, intermittently performed so that the laminate W alternately has stretch regions and bonded regions.

Instead of providing the detector 11 of FIG. 1B, an operator may visually judge a state of the initially formed part M1 and operate the cutter 7 to cut, remove and discard the pre-elastomer M in an initial state of production after the start of discharge of the pre-elastomer M.

Further, in this embodiment, the cutter 7 operates to cut the initially formed part M1 by the blade 70 after the elapse of the certain time following the detection of the initially formed part M1 of the pre-elastomer M by the detector 11. However, the cutter 7 may be manually or automatically operated to cut the pre-elastomer M, for example, when abnormal winding on the outer peripheral surface of the first cooling roll T1 or the second cooling roll T2 is detected or visually discovered.

Although the preferred embodiment has been described above with reference to the drawings, a person skilled in the art would easily arrive at various changes and modifications within an obvious range through this specification.

For example, one cooling roll may be provided. Further, the pre-elastomer may be cooled by air without providing any cooling roll.

Therefore, such changes and modifications are interpreted to be within the scope of the present invention determined from claims.

INDUSTRIAL APPLICABILITY

The present invention can be utilized in the manufacturing of a laminate for a wearable article such as a disposable diaper.

LIST OF REFERENCE SIGNS

1: first sheet pass line, 1A: second sheet pass line
2: laminate pass line, 3: film pass line
4: guider, 5 cylinder, 6: slide base, 7 cutter, 70: blade
10: control device, 11: detector, 12: moving device, 13: frame 21: first roll, 22: second roll.
F: elastomer film (example of thermoplastic film)
M pre-elastomer (example of film raw material), M1 initially formed part
S1: first sheet, S2: second sheet, W: laminate
E: tip part
Ar: bonding roll, H: horn, Nr: nip roll
P1: retracted position, P2: contact position
T: discharger, TO: discharge port
T1: first cooling roll, T2: second cooling roll

The invention claimed is:

1. A manufacturing apparatus for manufacturing a laminate by laminating a thermoplastic film on a sheet at a joining part after a pass line forming process of forming a pass line for a film-formed film raw material, the film raw material becoming the thermoplastic film, the manufacturing apparatus comprising:
 a discharger for causing a resin in a molten state to hang down from a discharge port, the resin becoming the film raw material, and the discharger continuously discharging the film raw material;
 a cutter for cutting off an initially formed part of the film raw material so as to form a tip part of the film raw material, the initially formed part being removed from the tip part;
 wherein the cutter cuts off the initially formed part by moving across an entire width of the initially formed part;
 a sheet pass line for receiving the tip part of the film raw material with the sheet and conveying the sheet and the film raw material in a mutually overlapping state after the tip part overlaps the sheet; and
 the joining part configured such that the sheet and the film raw material in the mutually overlapping state are introduced to the joining part from the sheet pass line.

2. The manufacturing apparatus according to claim 1, wherein the thermoplastic film is an elastomer film and the film raw material is a film-formed pre-elastomer.

3. The manufacturing apparatus according to claim 2, wherein the cutter includes a blade configured to move in a width direction of the pre-elastomer to cut off the initially formed part.

4. The manufacturing apparatus according to claim 3, further comprising a moving device for moving the sheet pass line between a retracted position where the sheet pass line does not contact the initially formed part and a contact position where the tip part of the pre-elastomer contacts the sheet on the sheet pass line and the tip part and the sheet overlap with each other.

5. The manufacturing apparatus according to claim 4, further comprising a control device for moving the sheet pass line at the retracted position to the contact position after detecting the removal of the initially formed part having been cut.

6. The manufacturing apparatus according to claim 2, wherein the laminate is produced at the joining part by bonding the elastomer film, obtained by solidifying the pre-elastomer, to the sheet.

7. The manufacturing apparatus according to claim 6, wherein the sheet and the elastomer film are conveyed in an overlapping manner along an outer peripheral surface of a bonding roll, and the bonding roll constitutes at least a part of the joining part.

* * * * *